US012200425B2

(12) United States Patent
Merca et al.

(10) Patent No.: US 12,200,425 B2
(45) Date of Patent: Jan. 14, 2025

(54) HEARING DEVICE COMPRISING A RECEIVER MODULE COMPRISING A VENT HAVING A VENT VALVE DEVICE

(71) Applicant: GN Hearing A/S, Ballerup (DK)

(72) Inventors: Timea Denisa Merca, Ballerup (DK); Jan Johansen, Ballerup (DK)

(73) Assignee: GN HEARING A/S, Ballerup (DK)

( * ) Notice: Subject to any disclaimer, the term of this patent is extended or adjusted under 35 U.S.C. 154(b) by 109 days.

(21) Appl. No.: 17/705,265

(22) Filed: Mar. 25, 2022

(65) Prior Publication Data
US 2022/0360881 A1    Nov. 10, 2022

(30) Foreign Application Priority Data

May 6, 2021  (DK) ............................ PA202170214
May 6, 2021  (EP) .................................... 21172604

(51) Int. Cl.
*H04R 1/10* (2006.01)
*A61F 2/08* (2006.01)
(Continued)

(52) U.S. Cl.
CPC ......... *H04R 1/1041* (2013.01); *H04R 1/1016* (2013.01); *H04R 1/1083* (2013.01);
(Continued)

(58) Field of Classification Search
CPC .. H04R 1/1041; H04R 1/1016; H04R 1/1083; H04R 1/1091; H04R 3/005;
(Continued)

(56) References Cited

U.S. PATENT DOCUMENTS

| | | | |
|---|---|---|---|
| 2007/0114481 A1* | 5/2007 | Suyama | F16K 37/0091 123/506 |
| 2011/0019852 A1* | 1/2011 | Feucht | H04R 25/65 381/328 |

(Continued)

FOREIGN PATENT DOCUMENTS

| | | |
|---|---|---|
| EP | 2465270 | 6/2012 |
| EP | 3675524 | 7/2020 |

(Continued)

OTHER PUBLICATIONS

Extended European Search Report for EP Patent Appln. No. 21172604.7 dated Nov. 4, 2021.
(Continued)

*Primary Examiner* — Carolyn R Edwards
*Assistant Examiner* — Kuassi A Ganmavo
(74) *Attorney, Agent, or Firm* — Vista IP Law Group, LLP

(57) ABSTRACT

A hearing device comprises a receiver module for insertion into an ear canal of a user of the hearing device. The hearing device comprises a signal processor, and a controller. The receiver module comprises an output transducer, a vent having a vent valve device configured to open and close the vent. The controller is configured to electrically manipulate the vent valve device to be in a first position or in a second position based on a first signal received from the signal processor whereby the vent valve device is configured to move between the first position and the second position in response thereto. When the vent valve device enters/arrives in the first position a first sound is produced. When the vent valve device enters/arrives in the second position a second sound is produced. The first sound and/or the second sound are detectable by one or more input transducers.

26 Claims, 3 Drawing Sheets

(51) Int. Cl.
  *B08B 11/02* (2006.01)
  *G06F 3/16* (2006.01)
  *G10K 11/178* (2006.01)
  *H04R 3/00* (2006.01)
  *H04R 25/00* (2006.01)

(52) U.S. Cl.
  CPC ........... *H04R 1/1091* (2013.01); *H04R 3/005* (2013.01); *A61F 2/08* (2013.01); *B08B 11/02* (2013.01); *G06F 3/167* (2013.01); *G10K 11/17854* (2018.01); *G10K 11/17875* (2018.01); *G10K 11/17881* (2018.01); *H04R 25/30* (2013.01); *H04R 25/50* (2013.01); *H04R 25/556* (2013.01)

(58) Field of Classification Search
  CPC ...... H04R 25/556; H04R 25/30; H04R 25/50; H04R 25/558; B08B 11/02; A61F 2/08; G06F 2/08; G06F 3/167; G10K 11/17854; G10K 11/17875; G10K 11/17881
  See application file for complete search history.

(56) References Cited

U.S. PATENT DOCUMENTS

| | | | | |
|---|---|---|---|---|
| 2012/0082335 | A1* | 4/2012 | Duisters | H04R 1/1041 381/375 |
| 2012/0140963 | A1* | 6/2012 | Larsen | H02J 50/40 381/315 |
| 2014/0169579 | A1* | 6/2014 | Azmi | H04R 1/1083 381/71.6 |
| 2014/0169603 | A1* | 6/2014 | Sacha | H04R 25/652 381/324 |
| 2015/0092971 | A1* | 4/2015 | Kim | H04R 25/30 381/328 |
| 2015/0162770 | A1* | 6/2015 | Choi | B08B 1/04 34/88 |
| 2016/0150310 | A1* | 5/2016 | Bakalos | H04R 1/1041 381/372 |
| 2017/0167633 | A1* | 6/2017 | Birkelund | F16K 39/024 |
| 2018/0332408 | A1* | 11/2018 | Frei | H02J 7/0071 |
| 2019/0031401 | A1* | 1/2019 | Ramsuer | D06F 39/022 |
| 2019/0215620 | A1* | 7/2019 | Albahri | H04R 25/554 |
| 2019/0215621 | A1 | 7/2019 | Albahri et al. | |
| 2020/0213731 | A1* | 7/2020 | Miller | G10L 21/0232 |
| 2020/0260197 | A1* | 8/2020 | Thomsen | H04R 1/1041 |
| 2020/0288251 | A1* | 9/2020 | Kuipers | H04R 1/1041 |
| 2020/0314532 | A1* | 10/2020 | Kuipers | H04R 25/652 |
| 2020/0314561 | A1* | 10/2020 | El Guindi | H04R 25/554 |
| 2021/0092536 | A1* | 3/2021 | Roeck | H04R 25/603 |
| 2021/0409874 | A1* | 12/2021 | Lara-Quintanilla | H04R 9/025 |
| 2022/0417683 | A1* | 12/2022 | Braband | H04R 25/609 |

FOREIGN PATENT DOCUMENTS

| | | |
|---|---|---|
| EP | 3694227 | 8/2020 |
| EP | 3799443 | 3/2021 |
| GB | 2569536 | 6/2019 |
| WO | WO 2010140087 | 12/2010 |

OTHER PUBLICATIONS

1st Technical Exam Report dated Nov. 12, 2021 for Danish patent application No. PA 202170214.

* cited by examiner

HEARING DEVICE COMPRISING A RECEIVER MODULE COMPRISING A VENT HAVING A VENT VALVE DEVICE

RELATED APPLICATION DATA

This application claims priority to, and the benefit of, Danish Patent Application No. PA 202170214 filed on May 6, 2021, and European Patent Application No. 21172604.7 filed on May 6, 2021. The entire disclosures of the above applications are expressly incorporated by reference herein.

FIELD

The present disclosure relates to hearing devices. More specifically, the disclosure relates to a hearing device comprising a receiver module for insertion into an ear canal of a user of the hearing device. The receiver module comprises a vent having a vent valve device configured to open and close the vent.

BACKGROUND

A hearing device is an electronic device adapted for providing sound to, or alleviating a hearing loss of a person. There are different types of hearing devices. One common type of hearing devices are behind-the-ear (BTE) hearing devices which typically have a plug connector comprising an in-the-ear unit to be inserted into an ear canal of a user. Another type of hearing devices are in-the-ear (ITE) hearing devices which comprises an in-the-ear unit, configured to be inserted into an ear canal of a user. The in-the-ear unit typically comprise an speaker which amplifies sounds received by the microphones of the hearing device into the ear canal of the user.

However, such in-the-ear unit may become clogged by e.g. cerumen and skin particles falling off from the ear canal. Such clogging may affect the functionality of the hearing device and hence the lifetime of the hearing device. Therefore, there is a need for an improved hearing device that addresses the abovementioned problems.

SUMMARY

It is an object to provide an improved hearing device that improves functionality and lifetime of the receiver module of the hearing device.

It is another object to allow for monitoring functionality and cleaness of the receiver module of the hearing device.

It is a further object to allow for cleaning the receiver module

According to a first aspect, a hearing device is disclosed. The hearing devices comprises a receiver module for insertion into an ear canal of a user of the hearing device. The hearing device comprises a signal processor, and a controller. The receiver module comprises an output transducer, a vent having a vent valve device configured to open and close the vent. The controller of the hearing device is configured to electrically manipulate the vent valve device to be in a first position or in a second position based on a first signal received from the signal processor whereby the vent valve device is configured to move between the first position and the second position in response thereto. When the vent valve device enters/arrives in the first position a first sound is produced. When the vent valve device enters/arrives in the second position a second sound is produced. The first sound and/or the second sound are detectable by one or more input transducers.

Thereby, the controller of the hearing device, configured to electrically manipulate the vent valve device to be in the first position or in the second position based on the first signal received from the signal processor, allows for monitoring the vent valve device e.g. functionality and cleaness of the vent valve device. In addition, the controller of the hearing device may allow for moving potential obstacles, e.g. cerumen or skin particles falling off from the ear canal, from the vent e.g. from surfaces of a valve sealing in case a force applied by the vent valve device can move and push such potential obstacles from the vent. Thereby, such moving of the potential obstacles acts as a self-cleaning motion and hence increase the lifetime of the receiver module of the hearing device. Such potential obstacles may be moved away from the valve seat e.g. towards an outlet of the receiver module. The receiver module may comprise vent holes on its circumference. In this case, the potential obstacles may be moved out of the vent module via the vent holes on the circumference of the vent module. In any case, such potential obstacles may be captured by a dome geometry of the hearing device i.e. in a dome of the hearing device, and may be removed when the dome is exchanged or cleaned.

The controller of the hearing device may electrically manipulate the vent valve device to the first position or the second position a couple of times. Thereby, allowing for further moving potential obstacles from the vent.

In addition, the one or more input transducers allow for detecting the first sound and/or the second sound. On one hand, detection of the first sound and/or the second sound, by the one or more input transducers, indicates that the vent valve device is not clogged and is functioning properly. Thereby, no cleaning or at least no immediate cleaning is required and the user may continue using the hearing device. On the other hand, no detection of the first sound and/or the second sound, by one or more input transducers, indicates that the vent valve device is clogged i.e. not clean and is not functioning properly. It also means that the force applied by the vent valve device has not been able to move and push the potential obstacles from the vent. Thereby, the user may e.g. clean the receiver module or may run a checkup control, service, adjustment, refitting or diagnose.

In overall, the first aspect of the invention allows for monitoring the functionality and the cleanness of the receiver module and hence allows for increasing the lifetime of the receiver module. It also allows for cleaning the receiver module in the case when the force applied by the vent valve device can move and push the potential obstacles from the vent.

The receiver module may comprise a receiver housing. The receiver module may be connected to hearing device via e.g. a receiver wire. The receiver wire may be arranged at one end of the receiver housing. The receiver module may comprise a receiver sound outlet tube. The receiver module may be connected to one end of the receiver sound outlet tube at another end of the receiver housing. The other end of the receiver sound outlet tube may be held in place by a vent outlet.

By the vent is hereby meant a vent compartment comprising a vent valve device. The vent may be formed as a through-going canal in the body of the hearing device i.e. in the body of the receiver module of the hearing device. The vent may provide the hearing device with an acoustic path from the outside of the hearing device to the part residing within the ear canal of the user during use e.g. the receiver module. The vent may comprise a solenoid coil and a permanent magnet mounted on the vent valve device. The magnet may be a toroidal magnet. A plurality of vent inlets may be dispersed in the receiver housing wall between the solenoid coil and the vent outlet. The vent outlet may be embodied as a ring or inner bushel restricting the inner diameter of a proximal end of the receiver housing. A flange may be arranged at one end of the receiver housing. The flange may provide sealing between an ear plug and the receiver housing when the receiver housing is mounted in the ear plug. The vent valve device and the permanent magnet may be mounted together on the receiver sound outlet tube in a way that facilitates a sliding/moving motion of the vent valve device between the first e.g. open position and the second e.g. closed position. The sliding/moving motion may be initiated by applying an electric current to the solenoid coil for creating a magnetic field attracting or repelling the permanent magnet. An electric current through the solenoid coil in one direction may attract the permanent magnet, thereby opening the vent, and an electric current in the opposite direction through the solenoid coil may repel the permanent magnet, thereby closing the vent.

By the controller is hereby meant a vent valve device controller, configured to electrically manipulate the vent valve device.

The controller is configured to electrically manipulate the vent valve device to be in the first position or in the second position based on the first signal received from the signal processor. Electrically manipulate may mean to manipulate, move, affect etc. by means of an electrical signal.

By the vent valve device is hereby meant a movable component of the vent which is configured to open and close the vent. The vent valve device allows for pressure equalization between the ear canal and the surroundings. When the vent valve device opens the vent, there may be no occlusion and the user may hear sounds from the surroundings, so-called open fit. When the vent valve device closes the vent, there may be occlusion and the user may not hear sounds from the surroundings, so-called closed fit. The closed fit is desired e.g. when the user listens music or when the user has a phone call via an associated electronic device e.g. smart phone. The open fit or the closed fit may be selected by the user via the associated electronic device when desired.

By the first position or the second position is hereby meant an state where the vent is open or closed or vice versa. For instance, the first position may correspond to an state where the vent is open and the second position may correspond to an state where the vent is closed.

For example, in the open position of the vent valve device, the solenoid coil may attract the permanent magnet towards one end of the receiver housing. The open position may provide a passageway for air to flow between the plurality of vent inlets and the vent outlet. When the ear plug and the receiver housing is mounted in its intended place in the ear canal, the passageway may be the only way air can escape an ear canal, in the case that there is a sealing between the ear plug and the receiver housing.

Another example, in the closed position of the vent valve device, the solenoid coil may repel the permanent magnet towards another end of the receiver housing. The closed position may provide no passageway for air to flow between the plurality of vent inlets and the vent outlet i.e. the passageway may be closed. For instance, when an edge of the vent valve device abuts a rim of the vent outlet, the vent valve device and the vent outlet may form a seal trapping the air in the ear canal from the exterior.

When the vent valve device enters/arrives in the first position a first sound is produced. When the vent valve device enters/arrives in the first position, the vent valve device may hit a first limiting position, thereby the first sound is produced. Hence, the first sound is produced due to a physical collision between the vent valve device and the first limiting position of the vent. Thereby, the first sound represents that the vent valve device has arrived at the first limiting position. The first limiting position of the vent may be arranged inside a chamber of the vent at a first end. For instance, the vent valve device may move linearly or rotationally along a first direction inside the chamber of the vent until it hits the first limiting position at the first end. For example, the first sound may be produced when an edge of the vent valve device abuts a rim of the vent outlet. The first sound may be a first vibration pattern.

When the vent valve device enters/arrives in the second position a second sound is produced. When the vent valve device enters/arrives in the second position, the vent valve device may hit a second limiting position, thereby the second sound is produced. Hence, the second sound is produced due to a physical collision between the vent valve device and the second limiting position of the vent. Thereby, the second sound represents that the vent valve device has arrived the second limiting position. The second limiting position of the vent may be arranged inside the chamber of the vent at a second end. For instance, the vent valve device may move linearly or rotationally along a the direction inside the chamber of the vent until it hits the second limiting position. The second direction may be opposite to the first direction. For example, the second sound may be produced when the another edge of the vent valve device abuts a surface of the solenoid coil. The second sound may be a second vibration pattern. A sound level pressure range of each of the first sound and the second sound may be in the range of 20-110 dB. The sound level pressure ranges of the first sound and the second sound may be partially overlapped. The second sound may be different than the first sound. For example, the first sound level may be different than the second sound level. As an example, when the vent valve device is electrically manipulated using a power of 10 mW, the first sound level may be 90 dB(A) and the second sound level may be 105 dB(A) or vice versa.

The one or more input transducers may be vibration sensors e.g. a bone conducting sensor. The one or more input transducers may be part of the hearing device and may provide supplementary input signal to improve the overall signal-to-noise ratio (SNR).

The hearing device may be a headset, a hearing aid, a hearable etc. The hearing device may be an in-the-ear (ITE) hearing device, a receiver-in-ear (RIE) hearing device, a receiver-in-canal (RIC) hearing device, a microphone-and-receiver-in-ear (MaRIE) hearing device, a behind-the-ear (BTE) hearing device, an over-the-counter (OTC) hearing device etc, a one-size-fits-all hearing device etc.

The hearing device is configured to be worn by a user. The hearing device may be arranged at the user's ear, on the user's ear, in the user's ear, in the user's ear canal, behind the user's ear etc. The user may wear two hearing devices, one hearing device at each ear. The two hearing devices may be connected, such as wirelessly connected.

The hearing device may be configured for audio communication, e.g. enabling the user to listen to media, such as music or radio, and/or enabling the user to perform phone calls. The hearing device may be configured for performing hearing compensation for the user. The hearing device may be configured for performing noise cancellation etc.

The hearing device may comprise a RIE unit. The RIE unit typically comprises the earpiece such as a housing, a plug connector, and an electrical wire/tube connecting the plug connector and earpiece. The earpiece comprises a receiver module configured for being provided into an ear canal of a user, and an open or closed dome. The dome may support correct placement of the earpiece in the ear of the user. The RIE unit may comprise a microphone, a receiver, one or more sensors, and/or other electronics. Some electronic components may be placed in the earpiece, while other electronic components may be placed in the plug connector. The receiver may be with a different strength, i.e. low power, medium power, or high power. The electrical wire/tube provides an electrical connection between electronic components provided in the earpiece of the RIE unit and electronic components provided in the BTE unit. The electrical wire/tube as well as the RIE unit itself may have different lengths The hearing device may comprise at least an input transducer. The input transducer may be an external input transducer e.g. a microphone for picking up acoustic signals from the surroundings and converting the acoustic signals into electrical signals. The picked up acoustic signals may be analogue signals. The input transducer may be connected to an analog to digital (A/D) converter for converting the electrical signals from first input transducer into digital signals. All the signals may be sound signals or signals comprising information about sound. The hearing device may comprise more than one input transducer such as an internal input transducer. The internal input transducer may be arranged inside the receiver module of the hearing device.

The hearing device may comprises a signal processor. The one or more microphone output signals may be provided to the signal processor for processing the one or more microphone output signals. The signals may be processed such as to compensate for a user's hearing loss or hearing impairment. The signal processor may provide a modified signal. All these components may be comprised in a housing of an ITE unit or a BTE unit. The hearing device may comprise a receiver or output transducer or speaker or loudspeaker. The receiver may be connected to an output of the signal processor. The receiver may output the modified signal into the user's ear. The receiver, or a digital-to-analogue converter, may convert the modified signal, which is a digital signal, from the processor to an analogue signal. The receiver may be comprised in an ITE unit or in an earpiece, e.g. RIE unit or MaRIE unit. The hearing device may comprise more than one microphone, and the ITE unit or BTE unit may comprise at least one microphone and the RIE unit may also comprise at least one microphone.

The hearing device signal processor may comprise elements such as an amplifier, a compressor and/or a noise reduction system etc. The signal processor may be implemented in a signal-processing chip or a printed circuit board (PCB). The hearing device may further have a filter function, such as compensation filter for optimizing the output signal.

The hearing device may furthermore comprise a wireless communication unit or chip, such as a wireless communication circuit or a magnetic induction chip, for wireless data communication interconnected with an antenna, such as an radio frequency (RF) antenna or a magnetic induction antenna, for emission and reception of an electromagnetic field. The wireless communication unit including a radio or a transceiver, may connect to the hearing device signal processor and the antenna, for communicating with one or more external devices, such as one or more external electronic devices, including at least one smart phone, at least one tablet, at least one hearing accessory device, including at least one spouse microphone, remote control, audio testing device, etc., or, in some embodiments, with another hearing device, such as another hearing device located at another ear, typically in a binaural hearing device system.

According to a second aspect, a binaural system is disclosed. The binaural system comprises a first hearing device and a second hearing device according to the first aspect. The first sound and/or the second sound of the first or the second hearing device are detectable by the one or more input transducers in sequence with respect to one another. This aspect may generally present the same or corresponding advantages as the first aspect. In the binaural sysyem, the first hearing device is used in relation to one ear and the second hearing device is used in relation to another ear. In addition, the first sound and/or the second sound of the first or the second hearing device are detectable by the one or more input transducers in sequence with respect to one another. In other words, the one or more input transducers of the binaural system may detect the first and/or the second sound of the first or the second hearing device one after the one e.g. in a consecutive manner. Thereby, the first sound and/or the second sound of the first or the second hearing device are detected in a reliable manner and hence an improved binaural system is provided.

In some embodiments, the one or more input transducers may comprise a microphone or an array of microphones. The microphone or the array of the microphone may be any type of microphones compatible with the hearing devices. The microphone or the array of the microphone may be any type conventional and commercially available microphones, compatible with the hearing devices.

In some embodiments, at least one of the one or more input transducers may be arranged in the hearing device. Thereby, a more compact hearing device may be provided. For instance, the first input transducers of the hearing device which are compatible with the conventional design may be used as the one or more input transducers.

In some embodiments, at least one of the one or more input transducers may be arranged in the receiver module of the hearing device. Thereby, at least one of the one or more input transducers may be arranged closer to the vent valve device, allowing for e.g. a more sensitive hearing device. For example, at least one of the one or more input transducers may be arranged in front of the receiver module i.e. pointing towards the ear canal of the user when the user of the hearing device wears it in its intended position. Another example, at least one of the one or more input transducers may be arranged opposite to the receiver module i.e. pointing away from the ear canal of the user when the user of the hearing device wears it in its intended position. Thereby, at least one of the one or more input transducers may be arranged in flexible manner e.g. allowing for an improved design flexibility.

In some embodiments, the hearing device may be configured to be connected to a charging device. The at least one of the one or more input transducers may be arranged in the charging device. This may in turn allow for less contamination risk of the at least one of the one or more input transducers. This may also allow for a smaller and more compact receiver module, compared to the one or more input transducers being arranged in the receiver module. In addition, the at least one of the one or more input transducers may be used as a remote input transducer e.g. a remote microphone which may provide a directional input. The hearing device may be connected to the charging device for the purpose of being charged. It may also be that at least one of the one or more input transducers may be arranged in the hearing device and at least another one of the one or more input transducers may be arranged in charging device.

In some embodiments, the controller may be configured to electrically manipulate the vent valve device based on the first signal received from the signal processor, when the hearing device is in a charging mode. The hearing device may be in the charging mode when the hearing device is connected to the charging device. Thereby, in the charging mode, the sound from the movement of the vent valve device may not annoy the user, as the user may not be wearing the hearing device in the charging mode. This may in turn allow for a more user-friendly hearing device. In addition, when the hearing device is in the charging mode, the hearing device is connected to electricity and hence there may be no lack of battery power. Furthermore, when the hearing device is in the charging mode, the hearing device may by default be muted so there may be no other sounds to disturb when the one or more input transducers detect the first and/or second sound of the vent valve device.

In some embodiments, the controller may be configured to electrically manipulate the vent valve device based on the first signal received from the signal processor, at scheduled times. Thereby a more convenient and user-friendly hearing device may be provided. The scheduled times may be determined by the user of the hearing device. For instance, the user may select a scheduled time when the user does not use the hearing device such as midnight.

In some embodiments, the hearing device may further comprise a transceiver and an antenna. Thereby, the hearing device may become connected to an associated electronic device.

In some embodiments, if the first sound and/or the second sound is not detected by the at least one of the one or more input transducers or if the first sound and/or the second sound is below a predetermined threshold value, the signal processor may send a second signal via the transceiver and the antenna to an associated electronic device. This may in turn indicate that something blocks the vent valve device from moving to the first or the second position. By the first sound and/or the second sound being below a predetermined threshold value, it is hereby meant that the first sound and/or the second sound is detected. However, the detected sound is not as expected. For instance, the detected sound may not correlate with the predetermined threshold value. As an example, an amplitude of the detected sound may be below the amplitude of the predetermined threshold value. Another example, the vibration pattern of the detected sound may not correlate to a predetermined vibration pattern.

In some embodiments, the second signal sent via the transceiver and the antenna to the associated electronic device may comprise a notification to the user of the hearing device about a cleaning status of the receiver module. Thereby, the user of the hearing device may be notified about the cleaning status of the receiver module. Thereby, the user of the hearing device may monitor the functionality and cleanness of the receiver module of the hearing device. This may in turn allow the user to clean the receiver module or to run a checkup control, service, adjustment, refitting or diagnose. The notification may be any type of notification. For instance, the notification may be a text message or an audio signal shown on an application of the associated electronic device. The notification may also be sent from the charging device to the associated electronic device. For instance, the charging device may send a message to the associated electronic device. The notification may also be shown on the charging device. For instance, the charging device may comprise one or more light emitting diodes (LEDs). The one or more LEDs of the charging device may flash in a certain way to indicate the cleaning status of the receiver module. For example, the one or more LEDs may flash in green to indicate that the vent valve device of the receiver module is functioning properly and hence the receiver module is clean. Another example, the one or more LEDs may flash in red to indicate that the vent valve device of the receiver module is not functioning properly and hence the receiver module is not clean.

In some embodiments, the first sound and/or second sound may be defined by one or more of amplitude, frequency, timbre, envelope, velocity, wavelength and/or phase. The first sound may have a first range for one or more of the amplitude, frequency, timbre, envelope, velocity, wavelength and/or phase. Accordingly, the second sound may have a second range for one or more of the amplitude, frequency, timbre, envelope, velocity, wavelength and/or phase. The first range for at least one of the amplitude, frequency, timbre, envelope, velocity, wavelength and/or phase may be different than the second range. Thereby, the one or more input transducers may identify that the detected sound corresponds to the first or the second sound.

In some embodiments, the controller may be configured to electrically manipulate the vent valve device with an extra current to apply a higher force to move potential obstacles in the vent. This may in turn allow for more force i.e. higher force may be applied to the vent valve device. Thereby, the vent valve device may push and move away debris, and foreign objects e.g. cerumen or skin particles from the vent that may otherwise not be removed by the reference current. This may in turn facilitate the self-cleaning motion and may hence further increase the lifetime of the receiver module of the hearing device. By the extra current, it is hereby meant an extra current relative to a reference current. For instance, the extra current may be 50% to 200% higher than the reference current.

The present disclosure relates to different aspects including the device and the system described above and in the following, and corresponding device parts, each yielding one or more of the benefits and advantages described in connection with the first mentioned aspect, and each having one or more embodiments corresponding to the embodiments described in connection with the first mentioned aspect and/or disclosed in the appended claims.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
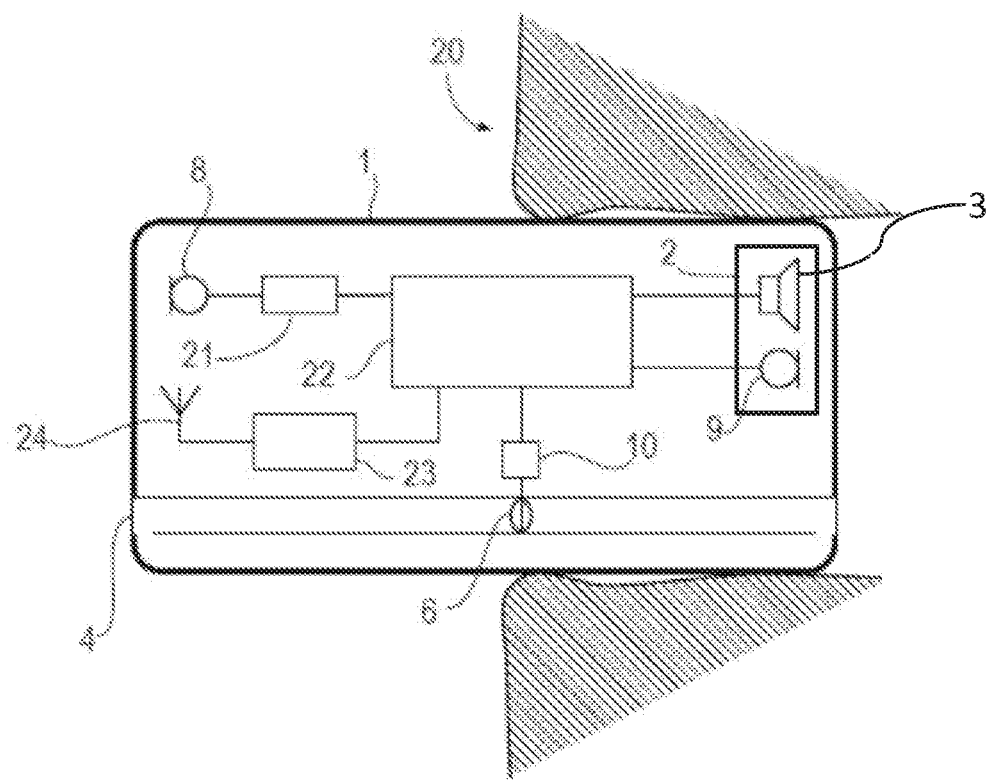
FIG. 1 schematically illustrates an exemplary block schematic of a hearing device comprising a receiver module.

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 schematically illustrates an exemplary block schematic of a hearing device 1 comprising a receiver module 2. The hearing device 1 shown in FIG. 1 is in the form of an in-the-ear unit of an in-the-ear (ITE) hearing device 1. However, it may be an in-the-ear unit i.e. an ear plug of a behind-the-ear (BTE) hearing device. During use, the in-the-ear unit of the hearing device is placed in an ear canal of a user and is held in place partly by the shape of part of a user's outer ear 20 and partly by the shape of the ear canal itself. FIG. 1 shows that the hearing device 1 comprises a receiver module 2 for insertion into an ear canal of a user of the hearing device 1.

In addition, FIG. 1 shows that the hearing device 1 comprises a signal processor 22 and a controller 10. The controller 10 may be a vent valve device controller. The hearing device, shown in FIG. 1, also comprises an external input transducer 8 for picking up acoustic signals from the surroundings and converting the acoustic signals into electrical signals. FIG. 1 shows that the external microphone 8 is connected to an analog to digital (A/D) converter 21 for converting the electrical signals from the external microphone 8 into digital signals. FIG. 1 shows that the hearing device 1 comprises a signal processor 22. FIG. 1 shows that the digital signals from the A/D converter 21 are output to a first input of a signal processor 22. The signal processor 22 may be adapted to provide amplification of the signals picked up by the external microphone 8 according to a hearing loss prescription for the purpose of alleviating a hearing loss of the user by performing various computational operations on the digital signals from the A/D converter 21. The amplified signals may be converted into a form suitable for being presented to the receiver module 2, which may be configured to convert the amplified signals into acoustic signals for the user to hear.

FIG. 1 also shows that the hearing device 1 comprises an antenna 24 and a transceiver 23 e.g. a wireless transceiver. The transceiver 23 may be configured to receive wireless signals picked up by the antenna 24 and may convert the wireless signals into electrical signals. The electrical signal may be fed to a second input of the signal processor 22. The wireless signals may e.g. be remote control signals or audio streaming signals intended for reproduction by the hearing device 1.

Figure 2:
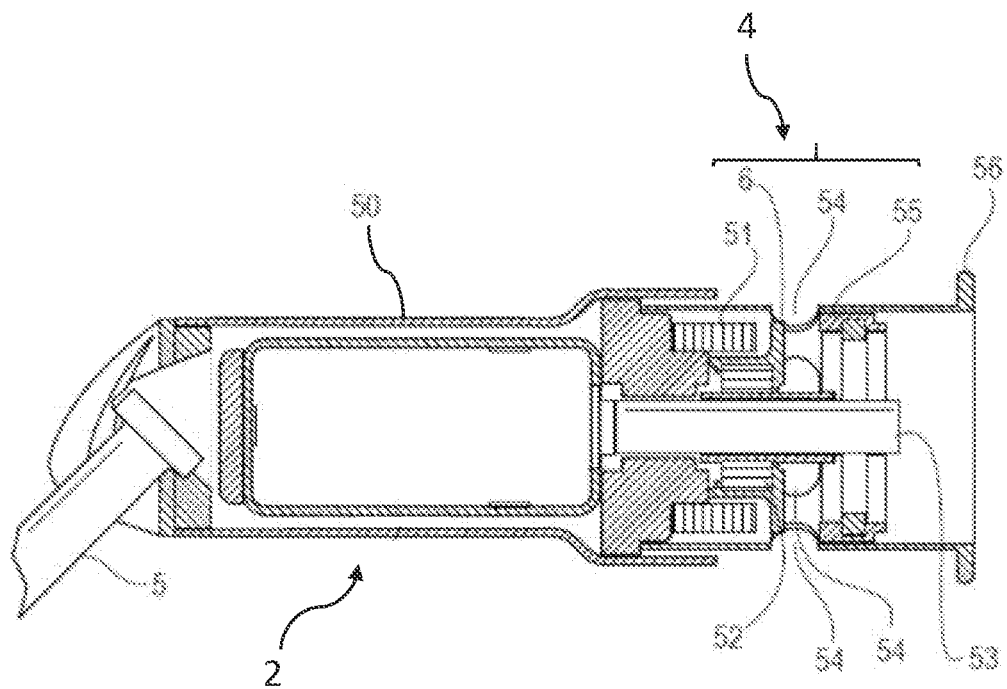
FIG. 2 schematically illustrates a longitudinal cut through a receiver module of a hearing device having a vent in an open position.
Figure 3:
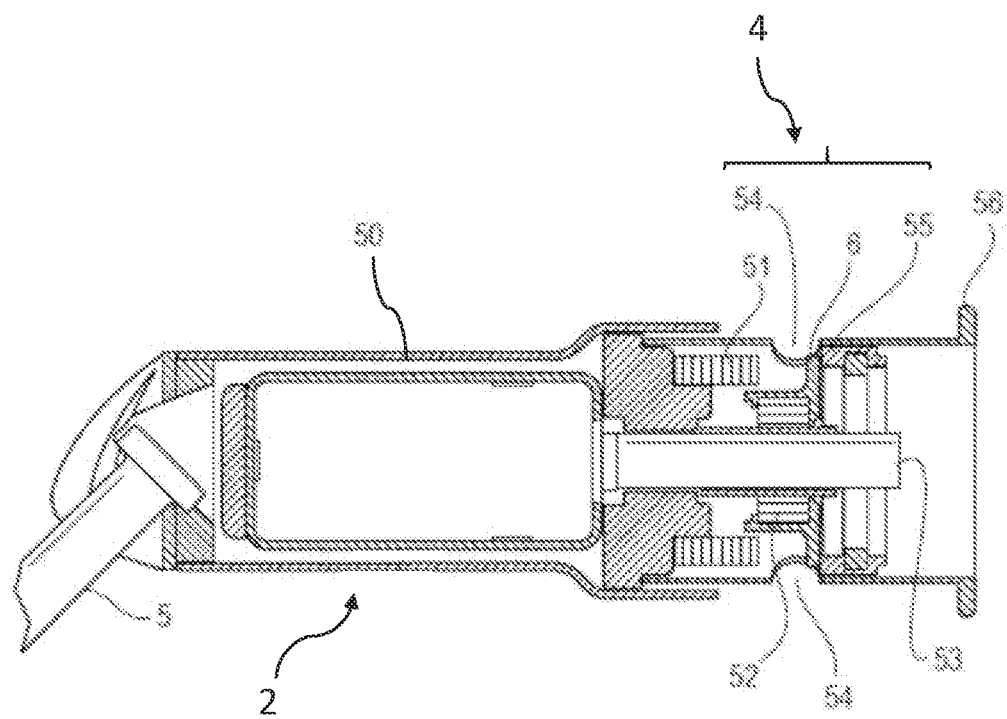
FIG. 3 schematically illustrates a longitudinal cut through the receiver module of the hearing device, shown in FIG. 2, having a vent in a closed position.

FIGS. 2 and 3 schematically illustrate a longitudinal cut through a receiver module 2 of a hearing device 1 having a vent in an open position and a closed position, respectively. The receiver module 2 comprises an output transducer 3, a vent 4 having a vent valve device 6. The vent 4, as also shown in FIG. 1, is formed as a through-going canal in the body of the hearing device 1 and provides the hearing device 1 with an acoustic path from the outside of the hearing device 1 to the part residing within the ear canal of the user during use e.g. the receiver module 2. The vent valve device 6 is configured to open and close the vent 4. The controller 10 of the hearing device 1 is configured to electrically manipulate the vent valve device 6 to be in a first position or in a second position based on a first signal received from the signal processor 22.

FIGS. 2 and 3 show that the receiver module comprises a receiver housing 50. The receiver housing 50 may have a substantially cylindrical shape. FIGS. 2 and 3 show that the receiver module 2 is connected to hearing device 1 via a receiver wire 5 at one end of the receiver housing 50. FIGS. 2 and 3 also show that the receiver module 2 is connected to one end of a receiver sound outlet tube 53 at another end of the receiver housing 50. The other end of the receiver sound outlet tube 53 may be held in place by a vent outlet 55.

FIGS. 2 and 3 also show that the vent 4 comprises a solenoid coil 51 and a permanent magnet 52 mounted on a vent valve device 6. The magnet 52 may be a toroidal magnet. A plurality of vent inlets 54 may be dispersed in the receiver housing wall between the solenoid coil 51 and the vent outlet 55. The vent outlet 55 may be embodied as a ring or inner bushel restricting the inner diameter of the proximal end of the receiver housing 50. A flange 56 may be arranged at one end of the receiver housing 50. The flange 56 may provide sealing between an ear plug (not shown) and the receiver housing 50 when the receiver housing 50 is mounted in the ear plug.

Still in connection with FIGS. 2 and 3, the vent valve device 6 is configured to move between the first position and the second position in response to the first signal received from the signal processor 22. The vent valve device 6 is configured to move between a first e.g. open position, shown in FIG. 2, and a second e.g. closed position, shown in FIG. 3. The vent valve device 6 and the permanent magnet 52 may be mounted together on the receiver sound outlet tube 53 in a way that facilitates a sliding/moving motion of the vent valve device 6 between the first, open position and the second, closed position. The sliding/moving motion may be initiated by applying an electric current to the solenoid coil 51 for creating a magnetic field attracting or repelling the permanent magnet 52. An electric current through the solenoid coil 51 in one direction may attract the permanent magnet 52, thereby opening the vent, and an electric current in the opposite direction through the solenoid coil 51 may repel the permanent magnet 52, thereby closing the vent.

FIG. 2 shows the open position of the vent valve device 6. In FIG. 2, the solenoid coil 51 has attracted the permanent magnet 52 towards the distal end of the receiver housing 50. The open position, shown in FIG. 2, provides a passageway for air to flow between the plurality of vent inlets 54 and the vent outlet 55. When the ear plug and the receiver housing 50 is mounted in its intended place in the ear canal, the passageway may be the only way air can escape an ear canal, in the case that there is a sealing between the ear plug (not shown) and the receiver housing 50.

FIG. 3 shows the closed position of the vent valve device 6. In FIG. 3, the solenoid coil 51 has repelled the permanent magnet 52 towards another end of the receiver housing 50. The closed position, shown in FIG. 3, provides no passageway for air to flow between the plurality of vent inlets 54 and the vent outlet 55 i.e. the passageway is closed. For instance, when the edge of the vent valve device 6 abuts a rim of the vent outlet 55, the vent valve device 6 and the vent outlet 55 forms a seal trapping the air in the ear canal from the exterior.

Still in connection with FIGS. 2 and 3, when the vent valve device 6 enters/arrives in the first position a first sound is produced. The vent valve device 6 may hit a first limiting position e.g. a first end stop, thereby the first sound is produced. For example, the first sound may be produced when the an edge of the vent valve device 6 abuts a rim of the vent outlet 55. When the vent valve device 6 enters/arrives in the second position a second sound is produced. The vent valve device 6 may hit a second limiting position e.g. a second end stop, thereby the second sound is produced. For example, the second sound may be produced when the another edge of the vent valve device abuts a surface of the solenoid coil. The first sound and/or second sound may be defined by one or more of amplitude, frequency, timbre, envelope, velocity, wavelength and/or phase.

Still in connection with FIGS. 2 and 3, the first sound and/or the second sound are detectable by one or more input transducers. The one or more input transducers 8, 9, 58, see FIGS. 1 and 5 may comprise a microphone or an array of microphones. At least one of the one or more input transducers 8, 9, 58 may be arranged in the hearing device 1. As shown in FIG. 1, an internal input transducer 9 and the external input transducer 8 are arranged in the hearing device 1. At least one of the one or more input transducers 8, 9, 58 may be arranged in the receiver module 2 of the hearing device 1. As shown in FIG. 1, the internal input transducer 9 is arranged in the receiver module 2 of the hearing device 1. If the first sound and/or the second sound is not detected by the at least one of the one or more input transducers 8, 9, 58 or if the first sound and/or the second sound is below a predetermined threshold value, the signal processor 22 may send a second signal via the transceiver 23 and the antenna 24 to an associated electronic device e.g. a smart phone. The second signal sent via the transceiver 23 and the antenna 24, see FIG. 1, to the associated electronic device may comprise a notification 62, 62', 62" to the user, see FIGS. 4 and 5, of the hearing device about a cleaning status of the receiver module 2. The notification 62, 62', 62" may be any type of notification. For instance, the notification 62, 62', 62" may be a text message or an audio signal shown on an application of the associated electronic device.

Figure 4:
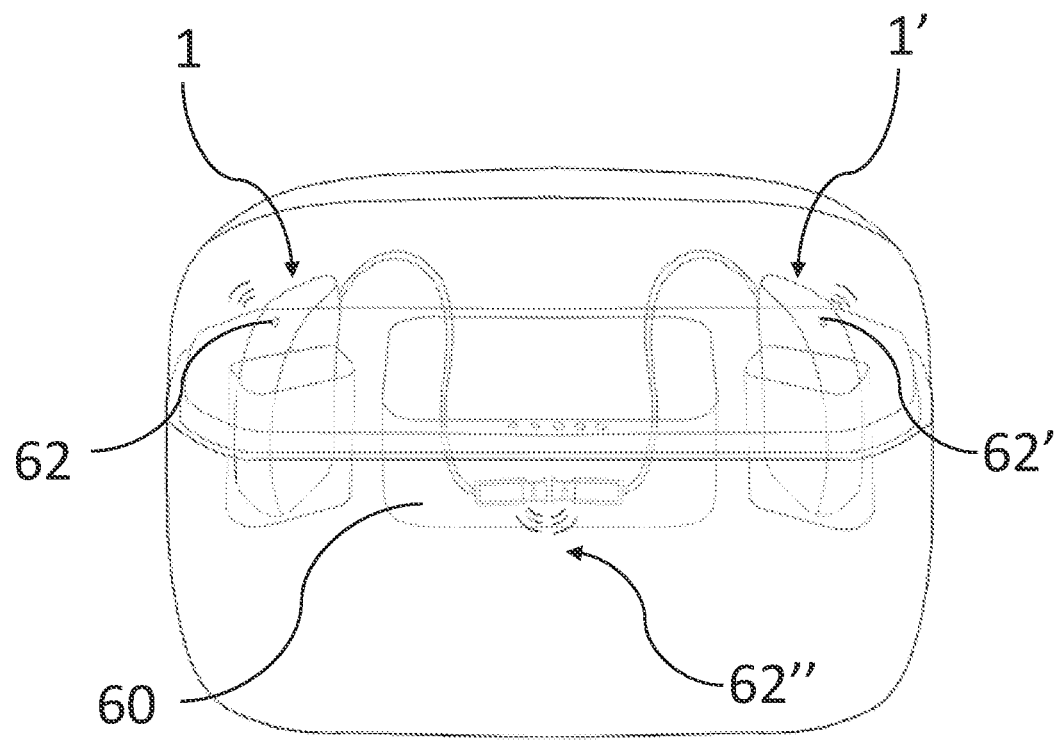
FIG. 4 schematically illustrates an exemplary binaural system comprising a first hearing device and a second earing device connected to a charging device.
Figure 5:
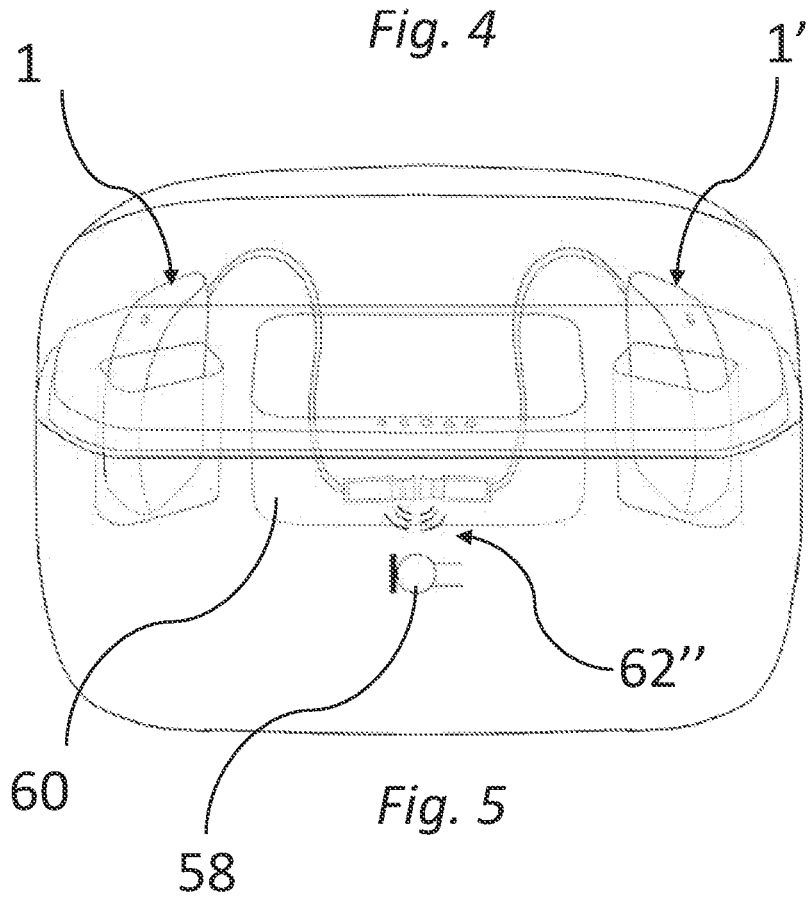
FIG. 5 schematically illustrates another exemplary binaural system comprising a first hearing device and a second earing device connected to a charging device, wherein at least one of the one of more input transducers is arranged in the charging device.

FIGS. 4 and 5 schematically illustrate a binaural system comprising a first hearing device 1 and a second hearing device 1' connected to a charging device 60. The first hearing device 1 and the second hearing device 1' may each be as the hearing device, described in relation to FIGS. 1-3. The first hearing device 1 and a second hearing device 1' may be configured to be connected to a charging device 60. FIG. 4 shows that the first hearing device 1 and the second hearing device 1' are connected to a charging device 60. The first sound and/or the second sound of the first or the second hearing device 1, 1' may be detectable by the one or more input transducers 8, 9, see FIG. 1, and/or 58 in sequence with respect to one another. The first sound and/or the second sound of the first or the second hearing device 1, 1' may be detectable by the at least one of the input transducers 8, 9 of the first and the second hearing devices 1, 1'. FIG. 4 shows the notifications 62, 62' sent respectively by the first hearing device 1 and the second hearing device 1'. FIG. 4 also shows the notification 62" sent by the charging device 60.

In connection with FIG. 5, at least one of the one or more input transducers 8, 9, 58 may be arranged in the charging device 60. FIG. 5 shows that the input transducers 58 is arranged in the charging device 60. The first sound and/or the second sound of the first or the second hearing device 1, 1' may be detectable by the one or more input transducers 8, 9, 58 in sequence with respect to one another. FIG. 5 shows that the first sound and/or the second sound of the first or the second hearing device 1, 1' are detectable by the input transducers 58 which is arranged in the charging device 60. The notification may be any type of notification. For instance, the notification may be an audio signal or an LED light shown on the charging device 60. FIG. 5 shows the notification 62" sent by the charging device 60. The notification may be sent from the charging device 60 to the associated electronic device. For instance, the charging device 60 may send a message to the associated electronic device.

Although particular features have been shown and described, it will be understood that they are not intended to limit the claimed invention, and it will be made obvious to those skilled in the art that various changes and modifications may be made without departing from the scope of the claimed invention. The specification and drawings are, accordingly to be regarded in an illustrative rather than restrictive sense. The claimed invention is intended to cover all alternatives, modifications and equivalents.

Items:

1. A hearing device (1) comprising a receiver module (2) for insertion into an ear canal of a user of the hearing device (1),
   the hearing device (1) comprising: a signal processor (22), and a controller (10),
   the receiver module (2) comprising: an output transducer (3), a vent (4) having a vent valve device (6) configured to open and close the vent (4),
   wherein the controller (10) of the hearing device (1) is configured to electrically manipulate the vent valve device (6) to be in a first position or in a second position based on a first signal received from the signal processor (22) whereby the vent valve device (6) is configured to move between the first position and the second position in response thereto,
   wherein when the vent valve device (6) enters/arrives in the first position a first sound is produced,
   wherein when the vent valve device (6) enters/arrives in the second position a second sound is produced, and
   wherein the first sound and/or the second sound are detectable by one or more input transducers (8, 9, 58).
2. The hearing device (1) according to item 1, wherein at least one of the one or more input transducers (8, 9, 58) is arranged in the hearing device (1).
3. The hearing device (1) according to item 1 or 2, wherein at least one of the one or more input transducers (8, 9, 58) is arranged in the receiver module (2) of the hearing device (1).
4. The hearing device (1) according to item 1, wherein the hearing device (1) is configured to be connected to a charging device (60) and wherein the at least one of the one or more input transducers (8, 9, 58) is arranged in the charging device (60).
5. The hearing device (1) according to any of the preceding items, wherein the controller (10) is configured to electrically manipulate the vent valve device (6) based on the first signal received from the signal processor (22), when the hearing device (1) is in a charging mode.
6. The hearing device (1) according to any of the preceding items, the hearing device (1) further comprising a transceiver (23) and an antenna (24).

7. The hearing device (1) according to any of the preceding items, wherein if the first sound and/or the second sound is not detected by the at least one of the one or more input transducers (8, 9, 58) or if the first sound and/or the second sound is below a predetermined threshold value, the signal processor (22) sends a second signal via the transceiver (23) and the antenna (24) to an associated electronic device.
8. The hearing device (1) according to any of the preceding items, wherein the second signal sent via the transceiver (23) and the antenna (24) to the associated electronic device comprises a notification to the user of the hearing device about a cleaning status of the receiver module (2).
9. The hearing device (1) according to any of the preceding items, wherein the first sound and/or second sound is defined by one or more of amplitude, frequency, timbre, envelope, velocity, wavelength and/or phase.
10. The hearing device (1) according to any of the preceding items, wherein the controller (10) is configured to electrically manipulate the vent valve device (6) with an extra current to apply a higher force to move potential obstacles in the vent (4).
11. The hearing device (1) according to any of the preceding items, wherein when the vent valve device (6) enters/arrives in the first position, the vent valve device (6) hits a first limiting position, thereby the first sound is produced and wherein when the vent valve device (6) enters/arrives in the second position, the vent valve device (6) hits a second limiting position, thereby the second sound is produced.
12. The hearing device (1) according to any of the preceding items, wherein the one or more input transducers (8, 9, 58) comprises a microphone or an array of microphones.
13. The hearing device (1) according to any of the preceding items, wherein the controller (10) is configured to electrically manipulate the vent valve device (6) based on the first signal received from the signal processor (22), at scheduled times.
14. A binaural system comprising a first hearing device (1) and a second hearing device (1') according to any of the preceding items, wherein the first sound and/or the second sound of the first or the second hearing device (1, 1') are detectable by the one or more input transducers (8, 9, 58) in sequence with respect to one another.

LIST OF REFERENCES

1, 1'. Hearing device
2. Receiver module
3. Output transducer
4. Vent
5. Receiver wire
6. Vent valve device
8. External input transducer
9. Internal input transducer
10. Controller
20. Part of outer ear
21. A/D converter
22. Signal processor
23. Transceiver
24. Antenna
50. Receiver housing
51. Solenoid coil
52. Toroidal magnet
53. Receiver sound outlet tube
54. Vent inlet
55. Vent outlet
56. Flange
58. Charging device input transducer
60. Charging device
62, 62', 62". Notification

The invention claimed is:

1. A hearing device comprising:
   a receiver module for insertion into an ear canal of a user of the hearing device, the receiver module comprising a housing having a distal end and a proximal end, and wherein the distal end of the housing is configured to face towards an environment of the user when the receiver module is inserted into the ear canal;
   a signal processor; and
   a controller;
   wherein the receiver module comprises an output transducer, a vent, and a vent valve device configured to open and close the vent;
   wherein the controller of the hearing device is configured to electrically manipulate the vent valve device to move the vent valve device to a first position or a second position based on a first signal received from the signal processor;
   wherein the hearing device is configured to provide a first sound when the vent valve is at the first position;
   wherein the hearing device is configured to provide a second sound when the vent valve device is at the second position;
   wherein the hearing device is configured to provide the first sound and/or the second sound for detection by one or more input transducers; and
   wherein an entirety of the vent valve device is inside the housing of the receiver module when the hearing device provides the first sound and when the hearing device provides the second sound, and wherein the vent valve device is closer to the proximal end of the housing than to the distal end of the housing when the hearing device provides the first sound and when the hearing device provides the second sound.

2. The hearing device according to claim 1, wherein the hearing device comprises at least one of the one or more input transducers.

3. The hearing device according to claim 1, wherein at least one of the one or more input transducers is in the receiver module of the hearing device.

4. The hearing device according to claim 1, wherein the hearing device is configured to be connected to a charging device, and wherein at least one of the one or more input transducers is in the charging device.

5. The hearing device according to claim 1, wherein the controller is configured to electrically manipulate the vent valve device based on the first signal received from the signal processor, when the hearing device is in a charging mode.

6. The hearing device according to claim 1, further comprising a transceiver and an antenna.

7. The hearing device according to claim 1, wherein the signal processor is configured to provide a second signal for transmission to an electronic device if the first sound and/or the second sound is not detected by at least one of the one or more input transducers, or if the first sound and/or the second sound is below a predetermind threshold value.

8. The hearing device according to claim 7, wherein the second signal comprises a notification for notifying the user of the hearing device about a condition of the receiver module.

9. The hearing device according to claim 8, wherein the condition of the receiver module comprises a cleaning status of the receiver module, and wherein the notification is for notifying the user of the hearing device about the cleaning status of the receiver module.

10. The hearing device according to claim 1, wherein one or each of the first sound and the second sound is defined by one or more of amplitude, frequency, timbre, envelope, velocity, wavelength and/or phase.

11. The hearing device according to claim 1, wherein the controller is configured to electrically manipulate the vent valve based on a reference current.

12. The hearing device according to claim 11, wherein the controller is configured to electrically manipulate the vent valve device with an extra current to apply a higher force to move the vent valve device.

13. The hearing device according to claim 1, wherein the vent valve device is configured to abut a stopper that defines one of the first position or the second position.

14. The hearing device according to claim 13, wherein the stopper comprises a rim of a vent outlet.

15. The hearing device according to claim 1, wherein the one or more input transducers comprises a microphone or an array of microphones.

16. The hearing device according to claim 1, wherein the controller is configured to electrically manipulate the vent valve device based on the first signal received from the signal processor, at a scheduled time.

17. The hearing device according to claim 1, wherein the first sound comprises a first vibration pattern.

18. The hearing device according to claim 1, wherein the hearing device is configured to provide the first sound and the second sound in sequence for detection by the one or more input transducers.

19. The hearing device according to claim 1, wherein the controller of the hearing device is configured to electrically manipulate the vent valve device to move the vent valve device between the first position and the second position.

20. A binaural system comprising the hearing device of claim 1, and an additional hearing device.

21. The hearing device according to claim 1, wherein the first sound is due to a physical collision that occurs in the hearing device.

22. The hearing device according to claim 21, wherein the physical collision is between the vent valve and a component of the hearing device, and occurs when the vent valve is at the first position.

23. The hearing device according to claim 22, wherein the component is configured to stop the vent valve at the first position.

24. The hearing device according to claim 1, wherein the second sound is due to a physical collision that occurs in the hearing device.

25. The hearing device according to claim 24, wherein the physical collision is between the vent valve and a component of the hearing device, and occurs when the vent valve is at the second position.

26. The hearing device according to claim 25, wherein the component is configured to stop the vent valve at the second position.

* * * * *